(12) United States Patent
Hixson, Sr.

(10) Patent No.: US 6,974,255 B1
(45) Date of Patent: Dec. 13, 2005

(54) MAMMOGRAPHIC PADDLE

(75) Inventor: Gordon L. Hixson, Sr., Chattanooga, TN (US)

(73) Assignee: American Mammographics, Inc., Chattanooga, TN (US)

( * ) Notice: Subject to any disclaimer, the term of this patent is extended or adjusted under 35 U.S.C. 154(b) by 113 days.

(21) Appl. No.: 10/634,315

(22) Filed: Aug. 5, 2003

Related U.S. Application Data

(60) Provisional application No. 60/406,564, filed on Aug. 28, 2002.

(51) Int. Cl.[7] .............................................. A61B 6/04
(52) U.S. Cl. ...................................... 378/208; 378/37
(58) Field of Search ........................ 378/37, 177, 204, 378/208; 128/845, 915; 600/407, 411, 423, 600/425, 426, 427, 439, 429

(56) References Cited

U.S. PATENT DOCUMENTS

| | | | | |
|---|---|---|---|---|
| 3,971,950 A | * | 7/1976 | Evans et al. | 378/37 |
| 4,943,986 A | * | 7/1990 | Barbarisi | 378/37 |
| 5,029,193 A | * | 7/1991 | Saffer | 378/37 |
| 5,474,072 A | * | 12/1995 | Shmulewitz | 378/37 |
| 5,506,877 A | * | 4/1996 | Niklason et al. | 378/37 |
| 5,594,769 A | * | 1/1997 | Pellegrino et al. | 378/37 |
| 5,706,327 A | * | 1/1998 | Adamkowski et al. | 378/37 |
| 5,851,180 A | * | 12/1998 | Crosby et al. | 600/407 |
| 6,577,703 B2 | * | 6/2003 | Lindstrom et al. | 378/37 |
| 6,647,089 B1 | * | 11/2003 | Virta et al. | 378/37 |

* cited by examiner

*Primary Examiner*—Allen C. Ho
(74) *Attorney, Agent, or Firm*—Stephen J. Stark; Miller & Martin PLLC

(57) ABSTRACT

A breast compression device for use with a conventional mammography system is disclosed. The device comprises a paddle support frame which is slidably connected to a conventional mammography system's compression paddle carriage. A mounting arm may be provided for attaching the paddle support frame to the mammography system. The device further comprises a compression surface having a chest wall end and a nipple end. The paddle support frame is located between the x-ray tube and the detector of the mammography system. The compression surface of the device is comprised of three angled segments which conform to the normal contours of the breast.

22 Claims, 3 Drawing Sheets

MAMMOGRAPHIC PADDLE

CLAIM OF PRIORITY

This application claims the benefit of U.S. Provisional Patent Application No. 60/406,564 filed Aug. 28, 2002.

BACKGROUND OF THE INVENTION

1. Field of the Invention

This invention relates to a mammography compression device, and more particularly to a compression paddle which provides a more uniform compression to a woman's breast while preventing too much compression at the chest wall and yet providing enough compression towards the nipple end of the breast.

2. Description of Related Art

Mammography systems utilize a compression paddle which is used to compress the breast of a patient intermediate a support plate and the compression paddle. Good compression of the breast is necessary for good quality mammographic images. Good compression spreads apart the breast structures which reduces superimposed structures and spreads apart the breast tissue permitting better visualization of abnormalities.

Good compression of the breast improves mammographic image quality in several ways. Breast thickness is decreased, reducing radiation exposure time. This can eliminate blurring of the image due to motion. Lower x-ray energy is required and this produces higher contrast images while limiting patient exposure to radiation.

In the most common prior art breast compression device, the compression paddle is rigidly fixed to a frame and positioned so as to have a single compression surface which parallels a breast support platform surface. These prior art compression devices used with conventional mammography systems produce non-uniform breast compression with the greatest compression closest to the chest wall and the least compression towards the nipple where the breast is not as thick. These compression paddles also unfortunately permit movement of the breast tissue in the mid breast and in the nipple end of the breast during imaging which causes blurring of the image, because of insufficient compression. Since exposure times are typically measured on the order of seconds, even though the patient may not move observably, small movement as well as the heart beating can blur images over time. Those images taken with longer exposure times, such as about two or more seconds, are particularly often adversely affected. Additionally, these prior art compression paddles can cause patient discomfort near the chest wall where the compression surface applies the greatest compression.

A number of other compression paddles have been developed in order to attempt to overcome some of the problems associated with the most common prior art design.

One prior art breast compression device has a single planar compression surface that is not used parallel to the an image detector. The apparatus comprises a compression paddle pivotally connected to a frame at a pivot point located between the chest wall end and the nipple end. The paddle may be positioned at one of a plurality of angles relative to the support surface. When the non-parallel planar surface is angled toward the nipple from the chest wall, the breast tissue can be squeezed or pushed out of the x-ray field back towards and effectively into the chest wall. The result is that tissue, which may contain a tumor is not imaged. Nevertheless, this design more effectively compresses the nipple end of the breast than the parallel planar surface. An example of this type may be seen in U.S. Pat. No. 5,706,327.

Another compression system is disclosed in U.S. Pat. No. 3,971,950 to Evans, Jul. 27, 1976. This patent discloses a mammographic compression and positioning device which is independent of the x-ray system. The compression surface of the paddle has a curved lower surface with both a concave and a convex surface. The position of the paddle is adjustable in a plurality of directions. These curves are not believed to optimally compress the breast as the nipple end of the breast is undercompressed due to the concave portion located above the nipple end. The chest wall end would also be undercompressed. An additional drawback would be the breast tissue at chest wall end would tend to be pushed back out of the field of view of the imager.

Another compression paddle system has a paddle which comes down at an angle. This was produced by Planmed of Helsinki, Finland. During the first phase of compression, the chest wall side of the upper paddle is angled toward the image detector at the start of compression. As the paddle descends and starts to compress the breast, the paddle begins to level out. At completion of the compression, the paddle is level or parallel to the image detector. Since the paddle is level at the end of the process, it is not believed to be optimally oriented to compress the breast.

Another known compression device for a mammography system is disclosed in U.S. Pat. No. 5,506,877. This patent discloses a compression paddle, which is pivotally connected within the support frame by a pivot connection. The pivot connection is located on a chest wall side of the support frame. The compression paddle is substantially horizontal to the detector and is rotatable around the pivot connection. During the initial compression the compression paddle begins substantially parallel to said detector. As force is applied the paddle angles toward the detector during final compression. The breast appears to dictate the angle of compression, not the radiologist in this design. Furthermore, due to the conical shape of the breast, during final compression the paddle will end up angled downwardly from the chest wall to the nipple thereby pushing the breast toward the chest wall, possibly pushing some of the breast out of an image.

Another known compression paddle system was produced by Trex Medical Corporation for Bennett Contour mammography systems (Trex Medical Corporation, Product Brochure, January 1997). This compression apparatus comprises a compression paddle pivotally connected to a frame at a pivot point located at the chest wall end. Rotation about the pivot point is allowed so that an operator may select the paddle angle. The paddle itself was comprised of two planar surfaces which meet at an angle of about nine degrees. The planar surface closest to the chest wall extends a length of about one inch away from the breast with the other planar surface extending from there past the nipple.

While the Bennett paddle achieves improved compression of the breast without significantly displacing any breast tissue backward out of the field of view at the chest wall end, this device still has a number of disadvantages. Specifically, the approximate 9° angle between the two planar surfaces is believed to be so great that it effectively forms a valley where the two angular surfaces meet. The breast located below this valley receives suboptimal compression in a zone where the largest percentage of cancers are detected. Almost one half of all breast cancers are located within the posterior one third of the breast which is where this "dead zone" occurs with the Bennett paddle. The breast is very thick in this area which in itself often makes good imaging difficult.

If there is suboptimal compression here, small cancers might not be detected. A need therefore exists to optimally compress the breast within this zone to remove this potential "dead zone" from images taken.

Another known compression device for a mammography system is disclosed in U.S. Pat. No. 5,851,180 to Crosby et al., Dec. 22, 1998. This patent discloses an apparatus having first and second compression surfaces that experience a lateral translation as they move towards one another. In addition, the first and second compression surfaces may be tilted slightly relative to a plane orthogonal to the patient's chest wall to enhance the traction effect on the breast.

While significant strides have been made to provide a good compression system, a need still exists to provide an optimum paddle design. There are over twenty-five different types of breast cancer and many more abnormalities which could be confused as cancer. It only takes finding one additional cancer which would otherwise elude detection and go unnoticed to make a huge difference in the life of that one individual.

SUMMARY OF THE INVENTION

Consequently, it is a primary object of the present invention to provide a mammographic paddle which may more effectively compress the mid breast and breast tissue toward the nipple end, while preventing slippage of breast tissue from the field of view of the detector towards the chest wall end.

It is another object of the invention to provide a device which provides more uniform compression for the entire breast.

Another object of the invention is to provide a compression paddle which provides a relatively uniform compression on breasts for a large percentage of the population.

Another object of the invention is to provide improved image quality and less patient discomfort.

Another object of the invention is to provide higher contrast images with better x-ray penetration and spreading apart of breast tissue thereby resulting in fewer superimposed structures and more lesion detections.

Another object of the invention is to increase patient comfort.

Yet another object of the present invention is to reduce the amount of radiation exposure to a patient.

Yet another object of the present invention is to reduce the number of additional problem solving views needed.

Accordingly, the present invention provides a paddle that has a compression surface, preferably none of which is parallel with the image detector, the compression surface comprising three angled planar segments which are believed to conform to the normal contours of the breast for a large percentage of the population.

Two of the angled segments are located near the chest wall end. A main object of these angled segments near the chest wall end, is to make initial compression contact with a breast pushing the imaged tissue downward out and forward toward the nipple end of a breast so that it will be included in the scope of the detection device at the chest wall end. The two slightly angled segments located near the chest wall end more effectively push the imaged tissue downward and outward toward the nipple end of the breast than one larger angled segment. The chest wall lip portion of this inventive device is essentially perpendicular to the image detector and the compression paddle of this inventive device is horizontally adjustable within a support frame.

Accordingly, a mammographic paddle is disclosed having three planar sections. A first planar section proximate to the chest wall preferably has a downward tilt of about 2° relative to a horizontal or about 92° from the chest wall lip of the paddle. The first planar segment extends about ¾ of an inch. The second planar segment is preferably angled about 2° relative to the first segment and extends for about half an inch. The remaining third segment preferably extends to the lip of the nipple end of the paddle. Accordingly, the third segment has a slope of about 6° relative to the chest wall lip of the paddle.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENTS

Figure 1:
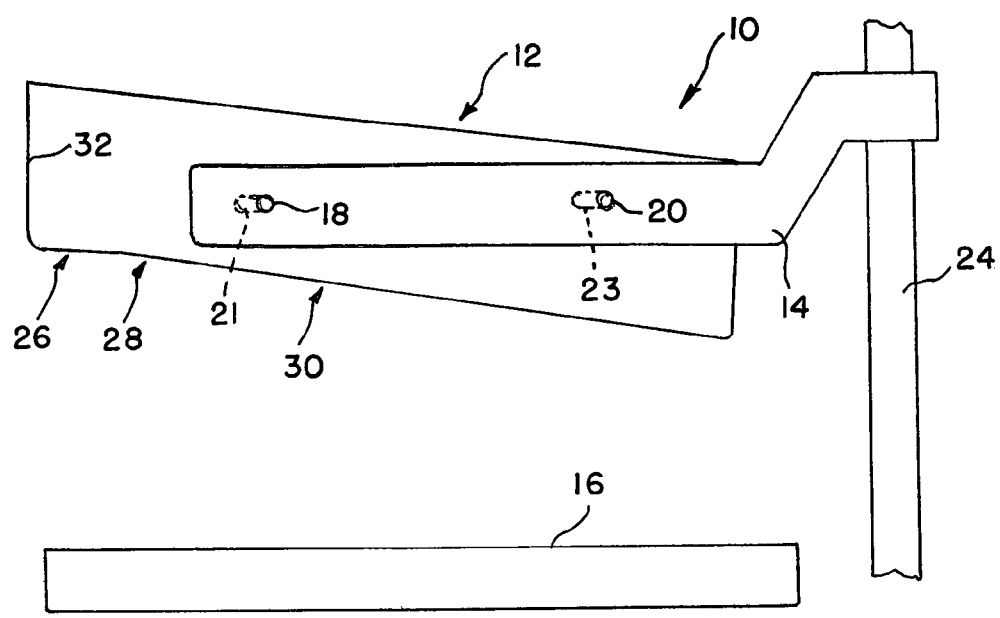
FIG. 1 is a side plan view of the preferred embodiment of the mammographic paddle of the present invention.

Accordingly, a compression system 10 of the preferred embodiment is illustrated in FIG. 1. The compression system includes a paddle 12 connected to a frame 14. This frame 14 is adjustable vertically relative to a support plate 16. An image detector (not shown) is typically located immediately below the support plate 16 or comprises a portion of the support plate 16. The compression system 10 shown in FIG. 1 shows a minimal number of components. Additional components known in the art and are shown in some of the references cited and are helpful in automating the compression system 10.

Figure 2:
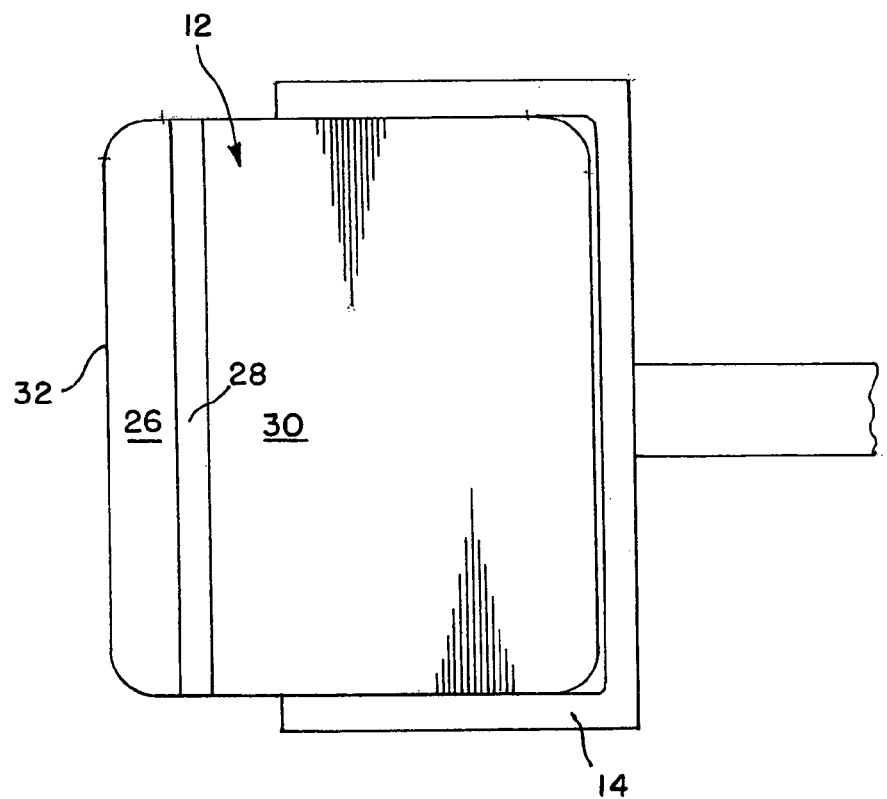
FIG. 2 is a top plan view of the paddle of FIG. 1.
Figure 3:
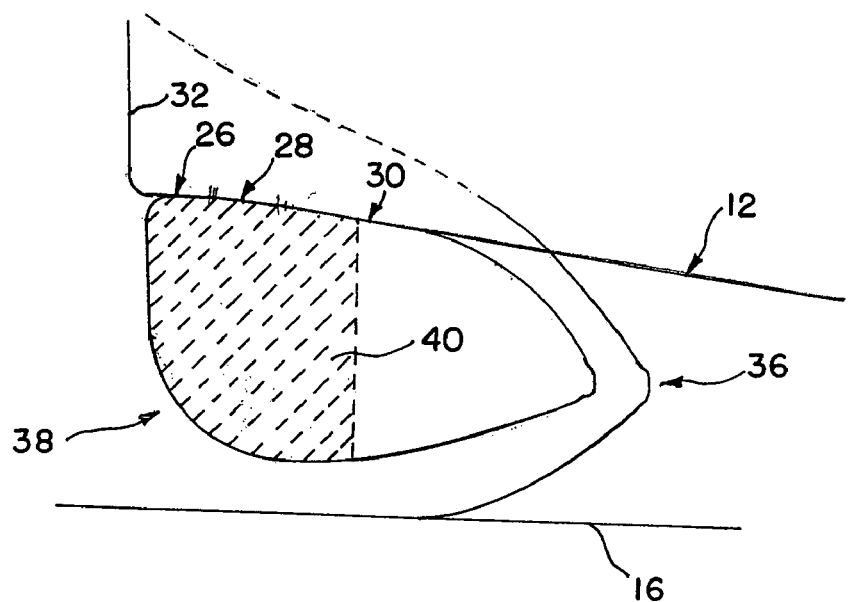
FIG. 3 is a cut away side view of a breast with the paddle compressing the breast for imaging.

FIG. 2 shows a top view of the paddle 12. The paddle 12 is connected to frame 14. Referring back to FIG. 1, the frame 14 is also vertically adjustable relative to guide 24 to selectively adjust the vertical position of the paddle 12 relative to the support plate 16. This way a breast 36 as shown in FIG. 3 may be compressed intermediate the paddle 12 and the support plate 16.

The paddle 12 is illustrated with three compression surfaces 26,28,30. Each of the compression surfaces 26,28,30 is planar. Preferably, the compression surfaces 26,28,30 are part of a molded piece of plastic which comprises the entire paddle 12.

The first compression surface 26 is preferably angled between about 90° to about 94° or 95°, and more preferably at about 92° relative to the lip 32. The lip 32 is preferably planar and placed against the chest wall of a patient above a breast. The first compression surface 26 preferably extends about an inch and preferably about ¾ of an inch away from the lip 32 and the chest end of the paddle 12. Accordingly, the lip 32 extends substantially perpendicularly to the support plate 16 which is usually positioned in a horizontal position such as parallel to the ground. The first compression surface 26 is preferably angled at about a 2° down angle relative to a parallel to the support plate 16 and/or a horizontal plane.

The second compression surface 28 is preferably an downwardly angled at about 2° relative to a plane extending through the first compression surface 26. Accordingly, there is an about 178° angle intermediate the first and second compression surfaces 26,28. Similarly, the third compression surface 30 is angled at about a 2° downward angle relative to a plane extending to the second compression surface 28. Accordingly, there is about a 178° angle intermediate the second and third compression surfaces 28,30. The second compression 28 surface is preferably on the order of about less than an inch and preferably about half an inch in length. These are small downward angles, i.e., less than 5° downward angles and preferably about 2°, relative to the respective planes. Four degrees and three degrees may be appropriate in other embodiments, but about two degrees has been found optimal in the preferred embodiment. The small downward angles are not present in the prior art and are believed to assist in optimally compressing the breast immediately beneath them, eliminating dead zones immediately beneath them while adequately compressing the mid breast and the nipple end.

As can be seen, the second compression surface 28 is angled at about a 4° down angle relative to a perpendicular through lip 32. The third compression surface is at about 6° downward angle relative to the perpendicular taken through the lip 32. Slots 21,23 in the paddle 12 allow for linear horizontal movement of the paddle 12 relative to frame 14. This provides for optimal alignment of the paddle 12 relative to the image detector and breast support plate 16 with a properly located compressed breast, intermediate the two. In the preferred embodiment, about ⅜ inch linear adjustment is provided through the use of slots 21,23 relative to pins 18,20.

It is preferable that the paddle 12 be fixed so that relative to the frame 14 so that the chest wall is substantially parallel to the lip 32, i.e., the lip 32 is substantially perpendicular to the horizontal and/or the support plate 16. Screws illustrated as pins 18,20 hold the paddle 12 relative to frame 14. Accordingly, the first compression surface 26 will have about a 2° down angle, the second compression surface 28 will have about a 4° down angle and the third compression surface 30 will have about a 6° down angle.

Figure 4:
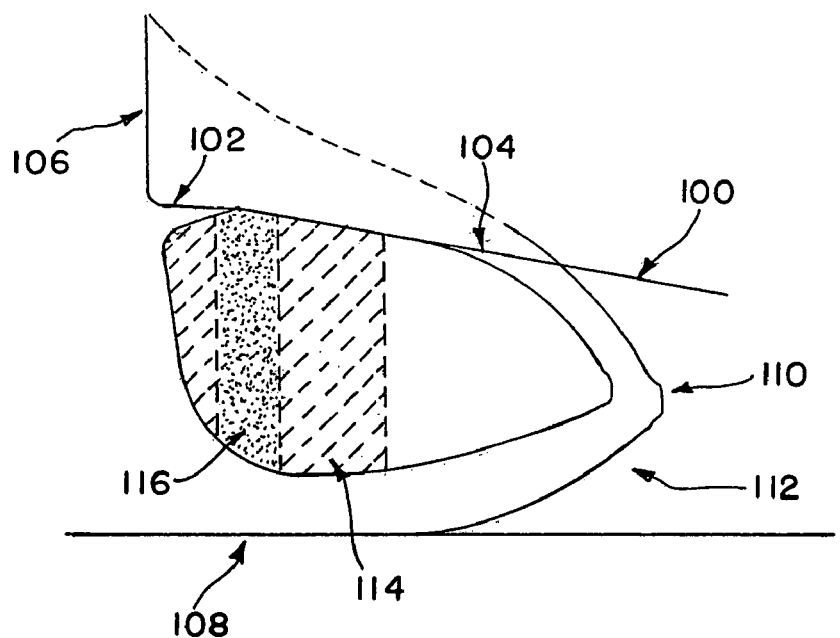
FIG. 4 is a prior art paddle illustrated compressing a breast.

FIG. 4 shows the use of a prior art Bennett paddle. The paddle 100 has two compression surfaces, the first compression surface 102 and a second compression surface 104. The first compression surface 102 is approximately perpendicular to the lip 106 of the paddle. The second compression surface 104 compresses the nipple end 110 of the breast 112 in a satisfactory manner in this design. However, since the majority of breast cancers occur in the zone 114 or 40 shown, i.e., the approximately posterior ½ of the breast. It is particularly important to image this zone, or area as clearly as possible. The known prior art of FIG. 4 has a dead zone in this area.

The first and second compression surfaces 102,104 meet at an angle of 8°–10° in the Bennett paddle 100. This angular displacement is believed to be so great that it creates a dead zone 116 shown within the common cancer zone 114 or 40 where breast compression is incomplete. Since some cancers could be as small as two tiny dots of calcium on an image, it could be possible to miss these two dots within the dead zone 116 even though the remainder of the breast 112 were adequately imaged. Accordingly, a need exists to improve over this prior art design.

FIG. 3 shows the preferred embodiment of the compression system 10 in operation. The slight downward angle of the first compression surface 26 is believed to adequately compress the breast 36 at the chest end 38 of the breast 36 without any significant backward displacement of breast tissue. This slight angle is relative to a horizontal plane extending through first compression surface 26.

The preferred downward angle of the second compression surface 28 relative to the first compression surface 26 is less than 5° and preferably about 2° so that the angle intermediate the first and second compression surfaces 26,28 is about 178°. The second compression surface 28 is preferably located entirely in the zone 40 or 114 where the highest percentage of cancers have been detected in women. At the end of the second compression surface 28, the third compression surface 30 begins and extends to the lip or nipple end of the paddle. Once again, the third compression surface 30 is angled at less than 5° and preferably at about 2° relative to a plane extending through the second compression surface 28. Accordingly, the second and third compression surfaces 28,30 meet at an angle of about 178°.

The use of the small or slight angles of downward displacement of the successive compression surfaces 26,28, 30 has been found to optimally compress all portions of the breast.

Figure 5:
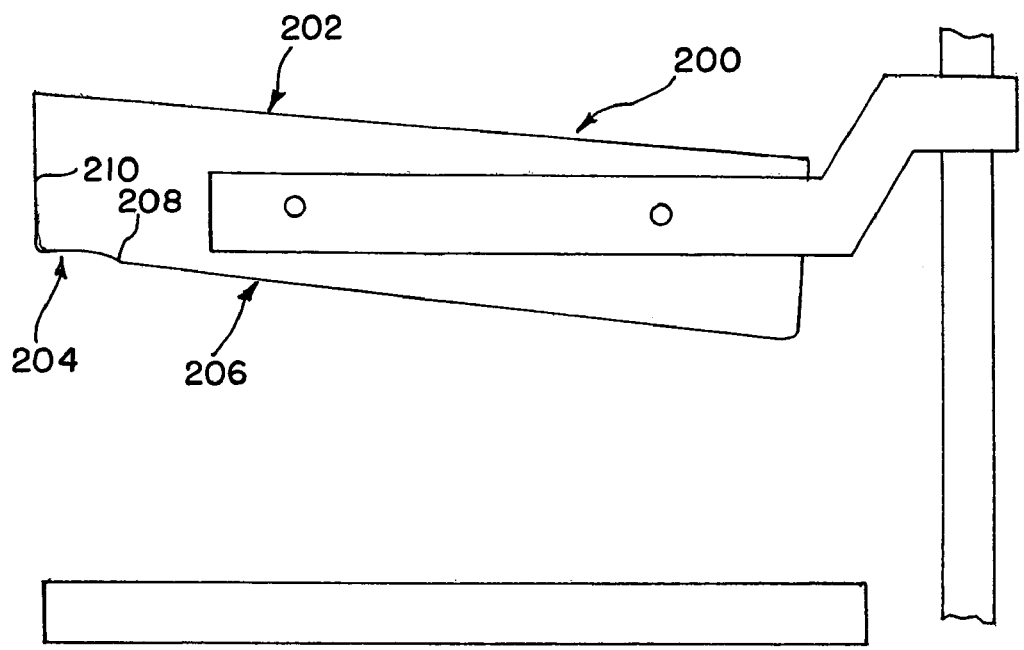
FIG. 5 is a first alternatively preferred embodiment of a paddle.

FIG. 5 shows an alternative embodiment of a compression system 200. The paddle 202 has slightly different construction than the preferred embodiment. The first compression surface 204 is a concave portion which meets a second compression surface 206 at transition point 208, illustrated. The concave portion of first compression surface 204 preferably has a radius of about 5 inches, however, parabolic curves or other curved shapes may be utilized in other embodiments. The first compression surface 204 begins at the lip 210 or chest wall and extends no more than 2 inches from the chest wall or lip 210, and preferably about an inch and a half, about an inch or even a half inch from the lip 210. A plane along the second compression surface preferably forms an angle with the lip 210 between about 90 to about 98 degrees.

Figure 6:
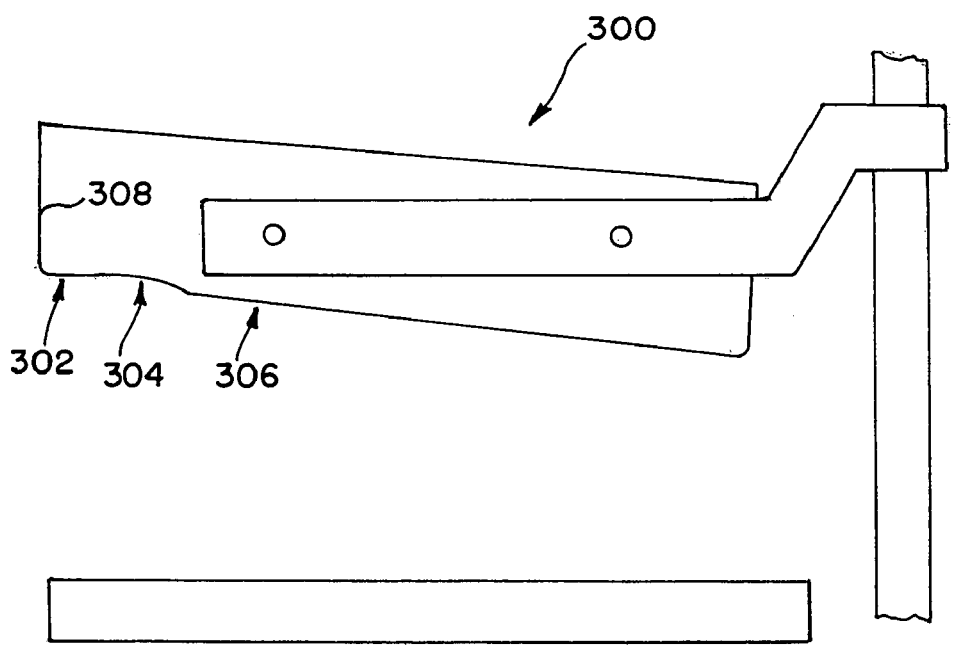
FIG. 6 is a second alternatively preferred embodiment of a paddle.

The second alternatively preferred embodiment of a paddle 300 is illustrated in FIG. 6. In this embodiment, a first planar compression surface 302 is illustrated connected to a second concave compression surface 304 which is connected to a third planar compression surface 306. The first planar compression surface 302 is adjacent to lip 308. The principal difference between this embodiment and the preferred embodiment is that the second compression surface 304 is not planar this embodiment but instead is curved such as a curve having a radius of approximately 5 inches. Of course, the radial curvature need not be constant across the compression surface 304 as it could be parabolic or some other form of curved shape.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A mammographic compression device comprising:
   a substantially planar image detector extending along a horizontal plane;

a compression paddle selectively moveable vertically toward and away from the image detector along a guide, said compression paddle having
　a first planar compression surface extending from a chest wall end of the compression paddle, said first planar compression surface extending less than about one inch from the chest wall end;
　a third compression surface spaced no more than an inch from the first planar compression surface, said third planar compression surface forming an angle relative to the first compression surface in a range of one hundred seventy three to one hundred seventy nine degrees; said third planar compression surface extending downwardly relative to the first planar compression surface toward the image detector.

2. The mammographic compression device of claim 1 further comprising:
　a second planar compression surface extending from the end of the first planar compression surface less than about one inch, said second planar compression surface forming an angle relative to the first compression surface of about one hundred seventy eight degrees; said second planar compression surface downwardly angled relative to the image detector.

3. The mammographic compression device of claim 2 wherein the second compression surface extends about one half inch intermediate the first and third compression surfaces.

4. The mammographic compression device of claim 1 further comprising a lip at a chest wall end of the compression paddle.

5. The mammographic compression device of claim 4 wherein the lip is planar and angled upwardly at about ninety two degrees relative to the first compression surface.

6. The mammographic compression device of claim 1 further comprising a frame connected to the compression paddle.

7. The mammographic compression device of claim 6 wherein the paddle is fixedly connected to the support frame.

8. The mammographic compression device of claim 1 wherein the first compression surface is angled downwardly at about a two degree down angle relative to a parallel plane to the image detector.

9. The mammographic compression device of claim 1 wherein the first compression surface extends about three quarters of an inch from the chest wall end of the compression paddle.

10. A mammographic compression device comprising:
　a breast support plate;
　a compression paddle moveable relative to the breast support plate, said compression paddle having a first compression surface beginning at a chest wall end of the paddle, said first compression surface being planar and extending less than about an inch away from the chest wall end of the paddle, a second compression surface being planar, angled at about one hundred seventy eight degrees relative to the first compression surface and extending less than about an inch, and a third compression surface angled downwardly relative to the second compression surface at about one hundred seventy eight degrees toward the breast support plate.

11. The device of claim 10 wherein the first compression surface is angled downwardly at about two degrees down from a horizontal plane.

12. The device of claim 11 wherein the compression paddle further comprises a lip at the chest wall end which extends substantially perpendicularly to the horizontal plane.

13. The device of claim 12 wherein the breast support plate is planar and located substantially perpendicularly to a plane extending through the lip of the paddle.

14. The device of claim 11 wherein the compression paddle is a formed plastic product.

15. The device of claim 10 further comprising a frame connected to the compression paddle, said frame imparting force to the compression paddle to compress a breast intermediate the paddle and the breast support plate.

16. The device of claim 15 wherein the frame is connected to sides of the paddle.

17. A mammographic compression device comprising:
　a substantially planar breast support plate extending along a horizontal plane;
　a compression paddle selectively moveable vertically toward and away from the breast support plate along a guide, said compression paddle having
　　a lip at a chest wall end of the compression paddle;
　　a first planar compression surface extending from the chest wall end of the compression paddle, said first planar compression surface extending less than about one inch from the chest wall end;
　　a second compression surface extending from the end of the first planar compression surface less than about one inch; and
　　a third planar compression surface extending from the end of the second planar compression surface to a nipple end of the compression paddle, said third planar compression surface forming an angle relative to the first compression surface in a range of one hundred seventy-three to one hundred seventy-nine degrees; said angle downwardly oriented toward the breast support plate.

18. The mammographic compression device of claim 17 wherein the second compression surface has a concave portion facing the breast support plate.

19. The mammographic compression device of claim 17 wherein the second compression surface is planar and the angle intermediate the first and second compression surfaces is about one hundred seventy eight degrees and downwardly oriented relative to the breast support plate.

20. A mammographic compression device comprising:
　a breast support plate; and
　a compression paddle having a lip at a chest wall end of the paddle, a first compression surface beginning at the chest wall end of the paddle, said first compression surface being concave relative to the breast support plate and extending less than about 2 inches from the chest wall end of the paddle, and a second planar compression surface extending from the first concave compression surface to a nipple end of the compression paddle wherein a plane extending through the second planar compression surface forms an angle with the lip of between about 92 and about 98 degrees so that the second planar compression surface is downwardly oriented toward the breast support plate relative to the first compression surface.

21. The mammographic compression device of claim 20 wherein the concave compression surface has a radius of about five inches.

22. The mammographic compression device of claim 20 wherein the concave compression surface is a parabolic curve.

* * * * *